(12) United States Patent
Chung et al.

(10) Patent No.: US 8,846,039 B2
(45) Date of Patent: Sep. 30, 2014

(54) METHOD FOR AMELIORATING PRURITUS

(75) Inventors: Yih-Lin Chung, Taipei (TW); Nam-Mew Pui, Taipei (TW); Wei-Wei Chang, Boston, MA (US)

(73) Assignee: Asan Laboratories Company (Cayman), Limited, Taipei (TW)

( * ) Notice: Subject to any disclaimer, the term of this patent is extended or adjusted under 35 U.S.C. 154(b) by 1132 days.

(21) Appl. No.: 11/848,272

(22) Filed: Aug. 31, 2007

(65) Prior Publication Data

US 2008/0107646 A1 May 8, 2008

Related U.S. Application Data

(63) Continuation-in-part of application No. 11/499,936, filed on Aug. 7, 2006, which is a continuation-in-part of application No. 10/798,119, filed on Mar. 11, 2004, which is a continuation-in-part of application No. 10/205,738, filed on Jul. 25, 2002, now Pat. No. 6,809,118, application No. 11/848,272, which is a continuation-in-part of application No. 10/843,025, filed on May 10, 2004, which is a continuation-in-part of application No. 10/205,738, filed on Jul. 25, 2002, now Pat. No. 6,809,118, application No. 11/848,272, which is a continuation-in-part of application No. 11/079,370, filed on Mar. 14, 2005, which is a continuation-in-part of application No. 10/132,999, filed on Apr. 26, 2002, now abandoned.

(51) Int. Cl.
| | |
|---|---|
| *A61K 39/395* | (2006.01) |
| *A61K 31/192* | (2006.01) |
| *A61K 31/19* | (2006.01) |
| *A61K 31/4355* | (2006.01) |
| *A61K 31/196* | (2006.01) |

(52) U.S. Cl.
CPC ............. *A61K 31/19* (2013.01); *A61K 31/192* (2013.01); *A61K 31/4355* (2013.01); *A61K 31/196* (2013.01)
USPC ........ 424/131.1; 514/282; 514/561; 514/557; 514/570; 514/569

(58) Field of Classification Search
CPC ............................................ A61F 2013/00276
USPC ........ 424/131.1; 514/282, 561, 557, 570, 569
See application file for complete search history.

(56) References Cited

U.S. PATENT DOCUMENTS

| | | | |
|---|---|---|---|
| 3,998,966 A * | 12/1976 | Fried et al. ................ | 514/510 |
| 5,281,623 A | 1/1994 | Clemens et al. | |
| 5,430,064 A | 7/1995 | Hirsch et al. | |
| 5,605,930 A | 2/1997 | Samid | |
| 5,877,213 A | 3/1999 | Samid | |
| 5,993,845 A | 11/1999 | Geerts et al. | |
| 6,093,740 A * | 7/2000 | Jirousek et al. ............ | 514/414 |
| 6,124,495 A | 9/2000 | Neiss et al. | |
| 6,225,294 B1 | 5/2001 | Daifotis et al. | |
| 6,313,091 B1 | 11/2001 | Wisniewski et al. | |
| 6,403,555 B1 | 6/2002 | Skov | |
| 6,538,030 B2 | 3/2003 | Chung et al. | |
| 6,548,479 B1 | 4/2003 | Skov | |
| 2001/0009922 A1 | 7/2001 | Faller | |
| 2001/0012513 A1 | 8/2001 | Robl et al. | |
| 2001/0021700 A1 | 9/2001 | Moore et al. | |
| 2002/0055542 A1 | 5/2002 | Chung et al. | |
| 2002/0183388 A1 | 12/2002 | Gudas et al. | |
| 2003/0082666 A1 | 5/2003 | Kammer et al. | |
| 2003/0114525 A1 | 6/2003 | Kammer et al. | |
| 2003/0134865 A1 | 7/2003 | Adcock et al. | |
| 2003/0147926 A1* | 8/2003 | Ebert et al. .................. | 424/400 |
| 2005/0171206 A1* | 8/2005 | Brahe et al. ................. | 514/570 |
| 2006/0251689 A1* | 11/2006 | Weidner ....................... | 424/401 |

FOREIGN PATENT DOCUMENTS

| | | |
|---|---|---|
| WO | WO 98/29109 | 9/1998 |
| WO | WO 01/17514 | 3/2001 |

OTHER PUBLICATIONS

U.S. Appl. No. 09/938,926, Chung et al.
ADR news, Phenytoin. Stevens-Johnson Syndrome: case report, Serious Reactions (ADR News), Feb. 22, 1996 ADISNEWS. See: abstract.
Danesi, Romano et al., "Pharmacogenetic Determinants of Anti-Cancer Drug Activity and Toxicity," *TRENDS in Pharmacological Sciences*, 22(8):420-426 and 420(Abstract, particularly) (2001).
Merck Index, Ninth Edition, 1976, pp. 137 and 1273.
Shufeng, Z., et al., "5,6-Dimethylxanthenone-4-acetic acid (DMXAA): A New Biological Response Modifier for Cancer Therapy," *Investigational New Drugs*, 20:281-295 (2002).
Goldman, Lee, et al., Cecil Textbook of Medicine, vol. 1, pp. 1061-1074, 21$^{st}$ed. (2000).
Mishra et al., "Histone Deacetylase Inhibitor Trichostatin A as a Strong Candidate for Treatment of Systemic Lupus Erythematosus," FASEB Journal, 5:A1214, Mar. 2001.
Mishra et al., "Trichostatin A Reverses Skewed Expression of CD154, Interleukin-10, and Interferon-Gamma Gene and Protein Expression in Lupus T Cells," Proceedings of the National Academy of Sciences of USA 98(5):2628-2633, (2001).

(Continued)

*Primary Examiner* — Jason Sims
*Assistant Examiner* — Ibrahim D Bori
(74) *Attorney, Agent, or Firm* — Cesari and McKenna, LLP (57) ABSTRACT

A method for preventing, treating, or ameliorating pruritus caused by skin, mucosa, or systemic disorder. The method comprises administering to a subject with pruritus or topically applying to an affected area with pruritus an effective amount of a formulation consisting essentially of a phenylbutyric acid or short-chain fatty acid derivative and a pharmaceutically acceptable carrier, salt or solvate thereof.

15 Claims, 7 Drawing Sheets

(56) References Cited

OTHER PUBLICATIONS

Richon et al., "Histone Deacetylase Inhibitor Selectively Induces P21 WAF1 Expression and Gene-Associated Histone Acetylation," PNAS, 97(18):10014-10019, Aug. 28, 2000.
Witt et al., "Induction of Fetal Hemoglobin Expression by the Histone Deacetylase Inhibitor Apicdin," Blood 101(5), Mar. 1, 2003.
www.merriam-webster.com/dictionary/prevent, Nov. 13, 2007.
Goldring et al., Mechanisms of Bone Loss in Inflammatory Arthritis: Diagnosis and Therapeutic Implications, Arthritis Res 2000, 2:33-37.
Stoilov et al.,"Inhibition of Repair of X-ray-induced DNA Double-Strand Breaks in Human Lymphocytes Exposed to Sodium Butyrate," *International Journal of Radiation Biology* vol. 76, No. 11, pp. 1485-1491 (2000).
Miller et al., "Modulation of Radiation Response of Human Tumour Cells by the Differentiation Inducers, Phenylacetate and Phenylbutyrate," *International Journal of Radiation Biology* vol. 72, No. 2, pp. 211-218 (1997).
Saunders et al., "Histone Deacetylase Inhibitors as Potential Anti-Skin Cancer Agents," *Cancer Research* vol. 59, pp. 399-404 (1999).
Chung et al. "Antitumor histone deacetylase inhibitors suppress cutaneous radiation syndrome: implications for increasing therapeutic gain in cancer radiotherapy" Molecular Cancer Therapeutics 2004;3(3):317-325.

\* cited by examiner

Gene Table

| BCL3 A01 | CCL11 A02 | CCL5 A03 | CCL7 A04 | CCR2 A05 | CCR3 A06 | CCR4 A07 | CCR5 A08 |
|---|---|---|---|---|---|---|---|
| CD80 B01 | CD86 B02 | CEBPB B03 | CREBBP B04 | CSF2 B05 | CTLA4 B06 | CXCR3 B07 | FASLG B08 |
| HAVCR2 C01 | ICOS C02 | IFNG C03 | IGSF6 C04 | IL10 C05 | IL12B C06 | IL12RB2 C07 | IL13 C08 |
| IL1R1 D01 | IL1R2 D02 | IL2 D03 | IL2R4 D04 | IL4 D05 | IL4R D06 | IL5 D07 | IL6 D08 |
| INHBA E01 | IRF1 E02 | IRF4 E03 | JAK1 E04 | JAK2 E05 | LAG3 E06 | LAT E07 | MAF E08 |
| NFATC2IP F01 | PCGF2 F02 | PTPRC F03 | SFTPD F04 | SOCS1 F05 | SOCS2 F06 | SOCS5 F07 | SPP1 F08 |
| TFCP2 G01 | TGFB3 G02 | TLR4 G03 | TLR6 G04 | TMED1 G05 | TNF G06 | CD27 G07 | TNFRSF8 G08 |
| B2M H01 | HPRT1 H02 | RPL13A H03 | GAPDH H04 | ACTB H05 | HGDC H06 | RTC H07 | RTC H08 |

FIG. 2D-1

| FIG. 2D-1 | FIG. 2D-2 |

| CD28 A09 | CD4 A10 | CD40LG A11 | CD69 A12 |
|---|---|---|---|
| GATA3 B09 | GFI1 B10 | GLMN B11 | GPR44 B12 |
| IL13RA1 C09 | IL15 C10 | IL18 C11 | IL18R1 C12 |
| IL6R D09 | IL7 D10 | IL9 D11 | INHA D12 |
| MAP2K7 E09 | MAPK8 E10 | NFATC1 E11 | NFATC2 E12 |
| STAT1 F09 | STAT4 F10 | STAT6 F11 | TBX21 F12 |
| TNFRSF9 G09 | TNFSF4 G10 | TYK2 G11 | YY1 G12 |
| RTC H09 | PPC H10 | PPC H11 | PPC H12 |

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gagttacttt tgtatcccca ccccc                                    25

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
cctgtacatt gtggcaggag ttgagg                                   26

METHOD FOR AMELIORATING PRURITUS

CROSS REFERENCE TO RELATED APPLICATIONS

This application is a Continuation-In-Part of pending U.S. patent application Ser. No. 11/499,936, filed on Aug. 7, 2006 and entitled "Method and compositions for treatment of epithelial damage", which is a Continuation-In-Part of pending U.S. patent application Ser. No. 10/798,119, filed on Mar. 11, 2004 and entitled "Method for increasing therapeutic gain in radiotherapy and chemotherapy", which is a Continuation-In-Part of U.S. patent application Ser. No. 10/205,738, filed on Jul. 25, 2002 (now U.S. Pat. No. 6,809,118) and entitled "Methods for therapy of radiation cutaneous syndrome"; a Continuation-In-Part of pending U.S. patent application Ser. No. 10/843,025, filed on May 10, 2004 and entitled "Histone hyperacetylating agents for promoting wound healing and preventing scar formation", which is a Continuation-In-Part of U.S. patent application Ser. No. 10/205,738, filed on Jul. 25, 2002 (now U.S. Pat. No. 6,809,118) and entitled "Methods for therapy of radiation cutaneous syndrome"; and a Continuation-in-part of Ser. No. 11/079,370, filed on Mar. 14, 2005 and entitled "Prevention of joint destruction", which is a Continuation-In-Part of Ser. No. 10/132,999, filed on Apr. 26, 2002 now abandoned and entitled "Methods for therapy of connective tissue disease".

BACKGROUND OF THE INVENTION

1. Field of the Invention

The present invention relates to a method for ameliorating pruritus, and in particular relates to a method of using a phenylbutyric acid or short-chain fatty acid derivative for preventing, treating, or ameliorating pruritus associated with localized or systemic diseases or disorders.

2. Description of the Related Art

As it is known, the cutaneous sensation referred to as pruritus, is characterized by an unpleasant, itchy sensation of the skin which provokes scratching. The scratching is sometimes severe enough to irritate and inflame the skin of afflicted subjects. Pruritus may also be characterized as a uniformed response to a wide variety of physical, chemical, and/or biological stimuli, which may be of an endogenous or exogenous nature that may be associated with specific dermatologic conditions such as allergic reactions to drugs, insect bites and to environmental allergens, or a systemic disease such as thyrotoxicosis, diabetes mellitus, uremia, iron deficiency anemia, delusions of parasitosis, polycythemia rubra vera, cholestasis and Hodgkin's disease. Although usually occurring in the skin, pruritus can also occur in non-cutaneous areas such as mucous membranes. Thus, the cause of pruritus can be multifactorial or due to a single underlying disorder. The pathophysiology of pruritus involves central and peripheral nervous systems as well as multiple cytokine release and molecular mediators.

When the origin of pruritus is in the skin, sensory nerve endings in the dermoepidermal junction are stimulated. The sensation of pruritus is transmitted along dedicated unmyelinated C fibers which are distinct from fibers that transmit pain and touch. The irritated skin will transmit the sensation of pruritus by stimulating local nerves in the spinal cord. From there, the stimulus travels via the lateral spinothalamic tract to the thalamus, and then on to the cerebral cortex, where it causes the sensation of pruritus (Weldon D. Allergy Asthma Proc 28: 153-62, 2007). Gastrin-releasing peptide receptor (GRPR), histamine, substance P, and tumor necrosis factor α (TNF-α) seem to play significant roles in the perception of pruritus (Sun Y G, et al. Nature 448:700-703, 2007). Moreover, for the central neural mechanism where itching is detected, the opioid peptides and the μ receptor have been implicated in provoking the pruritus of cholestasis, which responds to intravenous naloxone (Jones E A, et al. JAMA 268:3359-62, 1992). Meanwhile, serotonin reuptake inhibitors can improve systemic pruritus induced by cholestasis, suggesting that serotonergic pathways are also important in the perception of itching (Mayo M J, et al. Hepatology 45:666-74, 2007).

On the other hand, locally-released substances including histamine, tachykinins, serotonin (5-hydroxytryptamine (5-HT)), interferon (IFN)-gamma, interleukin 2 (IL-2) and IL-4 released from activated macrophage, mast or T cells at the site of pruritoceptive origin have been implicated to cause the symptoms and signs of itching sensation, scratching, swelling, rash, urticaria, and/or scaling (Greaves M W, et al. Lancet 348:938-40, 1996; Inagaki N, et al. Eur J Pharmacol 546:189-96, 2006). Subjects suffering from pruritus induced by a dermatological disorder or systemic disease can possibly worsen the pruritus by excessively scratching the affected area so extensively that the excessive scratching will lead to irritation, inflammation, wound formation and possibly infection. For the peripheral mechanism of pruritus, the role of multiple cytokine release and molecular mediators in the generation of signs and symptoms of pruritus in diseased skin or mucosa has been defined. Histamine-induced pruritus involves H1 receptors (Davies M G, et al. Br J Clin Pharmacol 9:461-65, 1980). Tachykinins including the neuropeptides substance P, calcitonin gene-related peptide, and vasoactive intestinal peptide are found in the cutaneous free-nerve endings of unmyelinated nociceptor neurons which initiate the sensations of pruritis. Intradermal 5-HT can evoke itching and scratching by acting on 5-HT2 and 5-HT3 receptors (Nojima H, et al. J Pharmacol Exp Ther 306:245-52, 2003). These observations have led to the use of a 5-HT2 or 5-HT3 receptor antagonist for treating pruritus (Schworer H, et al. Lancet 341:1277, 1993). IL-2 when given subcutaneously causes intense localized itching in both atopic and normal subjects (Wahlgren C F, et al. Arch Dermatol Res 287:572-80, 1995). Inhibition of IL-2 biosynthesis by immunosuppressive agents such as cyclosporine A relieves the pruritus of atopic dermatitis (Wahlgren C F, et al. Acta Derm Venereol (Stockh) 70:323-29, 1990).

Although antihistamines are widely used for suppression of pruritus, the extent to which suppression is attributable to the side-effect of central sedation rather than local histamine antagonism in the skin is unclear (Krause L, et al. BMJ 287:1199-200, 1983). Many patients report persistent pruritus even with current antihistamines therapies, 5-HT receptor antagonists, and/or immunosuppressive agents, as most are ineffective for chronic pruritus, and only provide short-term relief with side-effects. Pruritus may be quite debilitating for some patients. Thus, there is a continuing need for development of new and improved methods and compositions for preventing, treating, or ameliorating pruritus resulting from a wide variety of causes.

Phenylbutyrate, a short-chain fatty acid, has been approved by the FDA as an orphan drug for inborn error with urea cycle disorder to treat hyperammonemia (Brusilow S W, et al. N Engl J Med 310: 1630-4, 1984). In the human body, phenylbutyrate is metabolized to phenylacetate via β-oxidation. Phenylacetate subsequently undergoes conjugation with glutamine to form phenylacetylglutamine, which serves as a vehicle for waste nitrogen excretion. Recently, phenylbutyrate has also been found to have the ability to inhibit deacetylase, to increase acetylation on histones and non-histone proteins, to remodel chromatin structures and to alter activities of multiple transcriptional factors, resulting in simultaneously, epigenetically modulating many genes and thus, controlling diseases (Marks P A, et al. J Natl Cancer Inst 92: 1210-6, 2000). In preclinical and clinical studies, the gene modulatory effects of phenylbutyrate have exhibited therapeutic potential in many hematologic and solid tumors, inherited genetic disorders such as cystic fibrosis, sickle cell anemia, β-thalassemia, X-linked adrenoleukodystrophy, spinal muscular atrophy, and neurodegenerative disorders, aging, and inflammatory diseases such as autoimmune diseases (Kemp S, et al. Nat Med 4: 1261-8, 1998; et al. Proc Natl Acad Sci USA 102: 11023-8, 2005; Kang H L, et al. Proc Natl Acad Sci USA 99: 838-43, 2002; Blanchard F, et al. Drug Discov Today 10: 197-204, 2005). Moreover, phenylbutyrate can also act as a chemical chaperone to protect normal cells from oxidative stress injury and prevent neurotoxicity (Yam G H, et al. Invest Opthalmol V is Sci 48:1683-90, 2007).

BRIEF SUMMARY OF INVENTION

The invention provides a method of preventing, treating, or ameliorating pruritus associated with a cutaneous, mucosal or systemic disease or disorder, comprising administering to a subject with pruritus or topically applying to an affected area with pruritus an effective amount of a formulation comprising a phenylbutyric acid or short-chain fatty acid derivative and a pharmaceutically acceptable carrier, salt or solvate thereof.

The invention further provides a method of preventing, treating, or ameliorating pruritus associated with a cutaneous, mucosal or systemic disease or disorder, comprising administering to a subject with pruritus or topically applying to an affected area with pruritus an effective amount of a formulation comprising a phenylbutyric acid or short-chain fatty acid derivative of 2 to 6 carbons in length in combination with other anti-pruritic agents and a pharmaceutically acceptable carrier, salt or solvate thereof.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein:

FIGS. 2A-2C are human Th1-Th2-Th3 gene expression profiling demonstrating phenylbutyrate simultaneously suppressing the induction of multiple cytokine expression in activated T cells stimulated with PMA and ionomycin. Jurkat T cells were pre-incubated with phenylbutyrate (1 mM) for 24 hrs, and then stimulated with ionomycin (1 µM) and PMA (10 ng/ml) for 6 hrs. Using real-time PCR, the expression of a panel of genes related to helper T cells with or without T-cell stimulation and phenylbutyrate treatment was analyzed. The array includes cytokine genes representative of Th1, Th2 and Th3 cells, gene encoding transcriptional factors regulating the expression of cytokines as well as other markers of CD4+ T lymphocytes, genes involved in immune cell activation in the Th1 and Th2 type immune responses, and genes involved in the antimicrobial humoral response. Results are the mean ±SE of three determinations, expressed as the fold induction (observed experimental relative unit/basal control relative unit in the absence of any stimuli or treatment);

FIGS. 2D1-2D2 disclose the various human Th1-Th2-Th3 genes.

DETAILED DESCRIPTION OF INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention is broadly intended for use of phenylbutyric acid or a short-chain fatty acid and its pharmaceutically acceptable derivatives to prevent, treat or ameliorate all types of pruritus from various diseases or disorders including, but not limited to, allergic dermatoses, pruritic dermatoses, vascular dermatoses, sebaceous gland disorders, autoimmune disorders, rheumatoid arthritis, systemic lupus erythematosus, progressive systemic sclerosis, sjogren's syndrome, dermatomyositis, mixed connective tissue disease, papulosquamous dermatoses, bacterial dermatoses, viral dermatoses, mycolic skin infections, granulomatous dermatoses, parasitic skin dermatoses, exfoliative dermatitis, bullous dermatoses, pigmented dermatoses, photosensitive dermatoses, dermatoses caused by collagen diseases, dermatoses due to internal diseases, xerosis, urticaria, atopic dermatitis, eczyma, vasculitis, lichen simplex chronicus, psoriasis, scabies, pediculosis corporis and pubis, multiple sclerosis, thyrotoxicosis, diabetes, renal insufficiency, uremia, iron deficiency anemia, delusions of parasitosis, polycythemia rubra vera, cholestasis, wound, sun burn, cold sores, acne, insect bite, radiotherapy or chemotherapy-induced dermatitis or mucositis, paraneoplastic syndrome, malignancy, primary skin cancer, and metastatic skin cancer.

In the invention, the compounds of phenylbutyric acid derivatives include, but are not limited to, phenylbutyric acid, phenylproprionic acid, phenylacetic acid, phenylbutyrate, phenylproprionate, phenylacetate, phenylacetylglutamine, phenoxybutyric acid, phenoxyproprionic acid, phenoxyacetic acid, phenoxybutyrate, phenoxyproprionate, phenoxyacetate, bromophenylbutyric acid, bromophenylproprionic acid, bromophenylacetic acid, bromophenylbutyrate, bromophenylproprionate, bromophenylacetate, chlorophenylbutyric acid, chlorophenylproprionic acid, chlorophenylacetic acid, chlorophenylbutyrate, chlorophenylproprionate, chlorophenylacetate, fluorophenylbutyric acid, fluorophenylproprionic acid, fluorophenylacetic acid, fluorophenylbutyrate, fluorophenylproprionate, fluorophenylacetate, iodophenylbutyric acid, iodophenylproprionic acid, iodophenylacetic acid, iodophenylbutyrate, iodophenylproprionate, iodophenylacetate, hydroxyphenylbutyric acid, hydroxyphenylproprionic acid, hydroxyphenylacetic acid, hydroxyphenylbutyrate, hydroxyphenylproprionate, hydroxyphenylacetate, methylphenylbutyric acid, methylphenylproprionic acid, methylphenylacetic acid, methylphenylbutyrate, methylphenylproprionate, methylphenylacetate, ethylphenylbutyric acid, ethylphenylproprionic acid, ethylphenylacetic acid, ethylphenylbutyrate, ethylphenylproprionate, ethylphenylacetate, naphthylbutyric acid, naphthylproprionic acid, naphthylacetic acid, naphthylbutyrate, naphthylproprionate, naphthylacetate, and tributyrin. Also other short-chain fatty acids of 2 to 6 carbons in length include, but are not limited to, butyric acid, butyrate, 2,2 dimethyl butyric acid, α-methylhydrocinnamic acid, 3,5 dimethoxy-4-hydrocinnamic acid, cinnamic acid, butyryl hydroxamate, propionate, bromopropionate, E-3-3 pyridyl-2-propenoic acid, levulinic acid, Kemp triacid, isovalerate, valerate, butrymide, isobutyramide, valproic acid, and valproate.

The second compounds for combination with the phenylbutyric acid or short-chain fatty acid derivative include, but are not limited to, an anti-histamine, an anticholinergics, a non-steroid anti-inflammation drug, a steroid, an anti-oxidant agent, a vitamin, a leukotriene modifier, an interleukin antagonist, a mast cell inhibitor, an anti-IgE antibody, a selective serotonin reuptake inhibitor (SSRI), a 5-hydroxytryptamine (5-HT) receptor antagonist, an antibiotics, a calcineurin inhibitor, a histone deacetylase inhibitor, a gastrin-releasing peptide receptor antagonist, gabapentin, and naloxone.

The compounds of the invention can be formulated as pharmaceutical compositions. Such compositions can be administered orally, parenterally, by inhalation spray, rectally, vaginally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

In one embodiment, the preparations for treatment of skin pruritis are generally aimed at providing a condition for increasing skin manageability. There are recognized categories of formulations for skin care compositions, including creams, ointments, gels, sprays, lotions, skin tonics, shampoos or mousses as referred to above. Skin sprays are generally composed of aerosolized copolymers, such as polyvinylpyrrolidone, vinyl acetate and the like, and may also function as a setting lotion. Skin gel preparations are similar to sprays in composition, but are in gel and alcohol free form, and can coat the skin. Skin mousse is foam released under pressure from an aerosolized can. The phenylbutyric acid derivative or short-chain fatty acid active ingredient in a topical skin care composition according to the present invention is preferably present at a concentration of 0.00001 to 100.00% by weight relative to the total weight of the composition, or in a dosage of 1 to 1000 mg. A skin care composition for treating pruritus according to the present invention may be formulated as a hydrophobic or hydrophilic cream, ointment, gel, emollient, spray, lotion, skin tonic, shampoo or mousse as referred to above, suitably with additional ingredients suitable for use in skin care compositions of types known in the art, and such further ingredients can include petrolatum, waxes, lanolin, silicone, liposomes, vegetable, mineral oils, plasticizers, fragrances, preservatives, a penetration enhancing agent, a pH adjusting agent or other suitable ingredients for topical skin compositions. Such ingredients can moisturize skin, stabilize the active compound, increase drug-skin contact and local concentration, control drug slow release, and/or aid in decreasing skin breakage, preventing skin atrophy, fibrosis and infection, and promoting skin wound healing.

The invention also provides a method for treatment of skin pruritus as described herein, which method comprises a composition providing at least a phenylbutyric acid derivative or short-chain fatty acid thereof, together with at least one or more other agents, including an anti-histamine, an anticholinergics, a non-steroid anti-inflammation drug, a steroid, an anti-oxidant agent, a vitamin, a leukotriene modifier, an interleukin antagonist, a mast cell inhibitor, an anti-IgE antibody, a selective serotonin reuptake inhibitor, a 5-hydroxytryptamine receptor antagonist, an antibiotics, a calcineurin inhibitor, a histone deacetylase inhibitor, gabapentin, and naloxone, in which active ingredients are present in free form or in the form of a pharmaceutically acceptable salt and optionally at least one pharmaceutically acceptable carrier, for systemically or topically simultaneous, separate or sequential use.

Suitable salts for the components to be employed according to the present subject matter are also those with inorganic cations, for example alkali metal salts, in particular sodium, potassium, or ammonium salts, alkaline earth metal salts such as, in particular, the magnesium or calcium salts, as well as salts with bi- or tetravalent cations, for example the zinc, aluminum, or zirconium salts. Also contemplated are salts with organic bases, such as dicyclohexylamine salts; methyl-D-glucamine; and salts with amino acids, such as arginine, lysine, histidine, glutamine and so forth. Also, the basic nitrogen-containing groups can be quaternized with such agents as: lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others. Salt-forming agents, for example, low molecular weight alkylamines such as methylamine, ethylamine, or triethylamine can also be employed. Water or oil-soluble or dispersible products are thereby obtained.

The amount of active ingredient that can be combined with the carrier materials to produce a single dosage form will vary depending upon the subject and the particular mode of administration. The dosage required will vary according to a number of factors known to those skilled in the art, including, but not limited to, the compound or compounds used, the species of subject, the size of the subject, and the severity of the associated disease condition that causes pruritus. The compounds can be administered in a single dose, in multiple doses throughout a 24-hour period, or by continuous infusion. When administered by continuous infusion, the compounds can be supplied by methods well known in the art, such as, but not limited to, intravenous gravity drip, intravenous infusion pump, implantable infusion pump, or any topical routes. Length of treatment will vary depending on many factors, for example, the duration and severity of the skin, mucosa or systemic diseases or disorders that cause localized or generalized pruritus. Treatment of the subject with the phenylbutyric acid derivative or short-chain fatty acid derivative alone or in combination with other agents of the invention may last until pruritus disappears, or treatment will continue for the life of the subject.

EXAMPLE

Example 1

Various Topical Compositions-oleaginous Ointment, Cream and Gel

A. Preparation of an Oleaginous Ointment of Phenylbutyrate:

65 g of white petrolatum (Riedel-de Haen), 15 g of cetyl alcohol (Riedel-de Haen), 260 g of soft paraffin (Merck), 155 g of liquid paraffin (Merck), and 5 g of 4-phenylbutyrate (Merck) were mixed in a beaker and heated at 70° C. to form a paste. The paste was stirred at 400 rpm for 1 hour, and then cooled at room temperature.

B. Preparation of Cream of Phenylbutyrate:

Part I: 70 g of Tefose 63™, 20 g of Superpolystate™, 10 g of Coster 5000™, 15 g of Myriyol 318™, 15 g of Coster 5088™, and 15 g of GMS SE™ (all commercially available from a local supplier) were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), and 149.061 g of deionized water were mixed in a beaker and heated at 70° C.

Part II was slowly added into part I and continually stirred at 400 rpm for 5 minutes to form a mixture. 2% Stabileze QM™ (prepared by dissolving 2 g of Stabileze QM™ in 98 g of deionized water, heating and stirring at 70° C. to form a paste, and cooling at room temperature) was added into the mixture and stirred for 5 minutes. The pH of the mixture was adjusted to 5.34 with 0.85% phosphoric acid (Merck), and stirred at 600 rpm for 20 minutes. The mixture was cooled at room temperature.

C. Preparation of Gel of Phenylbutyrate:

Part I: 10 g of Stabileze QM™ and 232.035 g of deionized water were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), 232.035 g of deionized water, and 20 g of 10% NaOH were mixed in a beaker and heated at 70° C.

Part II was slowly added into part I and continually stirred at 400 rpm for 20 minutes to form a mixture. The mixture was cooled at room temperature.

D: Preparation of Liposomal Formulation of Phenylbutyrate:

In this liposomal formulation, egg phosphatidylcholine (EPC) and cholesterol were used in equi- or different-molar concentrations as primary lipid components. Various liposomes located with 4-phenylbutyrate were obtained by varying the lipid:phenylbutyrate ratio. Liposomes were prepared by thin film hydration, sized by membrane extrusion, and physically evaluated.

Example 2

Topical Phenylbutyric Acid to the Affected Skin of Different Disorders to Treat Pruritus A 2.5% phenylbutyric acid gel was applied to the affected skin six times per day for 1 week. There were four patients in each group, who completed a daily itch diary in which they graded the severity of their pruritus on a continuous scale from 0 (no pruritus) to 10 (the worse pruritus imaginable) using a visual analog scale (VAS) with points anchored with facial expressions to guide their selection (Mayo M J, et al. Hepatology 45:666-74, 2007).

Figure 1:
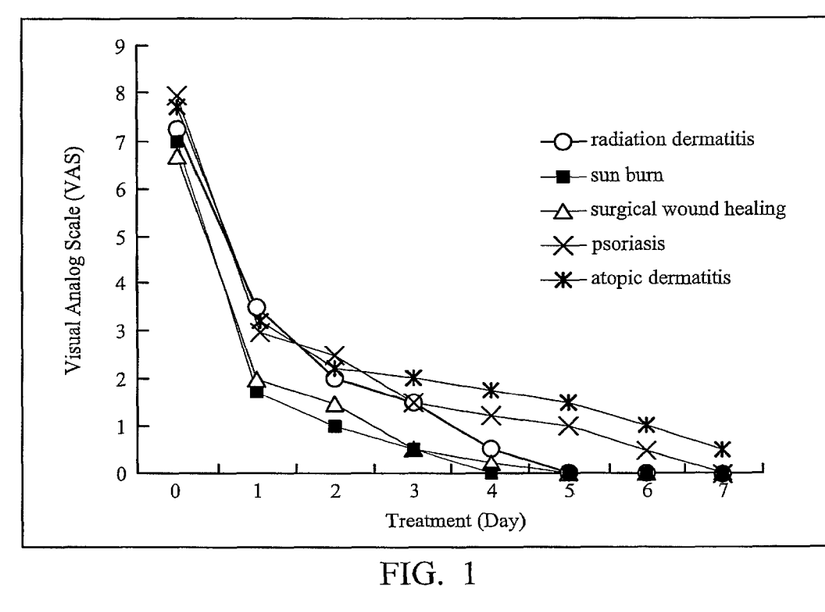
FIG. 1 shows a topical 2.5% phenylbutyric acid gel rapidly relieving pruritus associated with skin disorders caused by radiation dermatitis, sun burn, surgical wound healing, psoriasis, and atopic dermatitis.
Figure 2A:
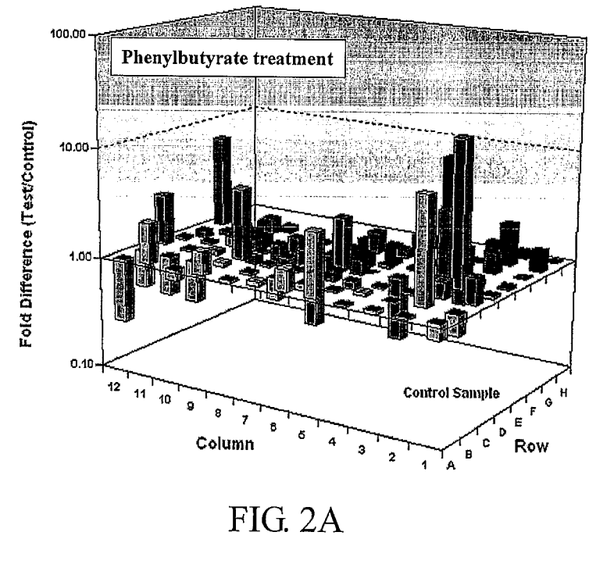
Figure 2B:
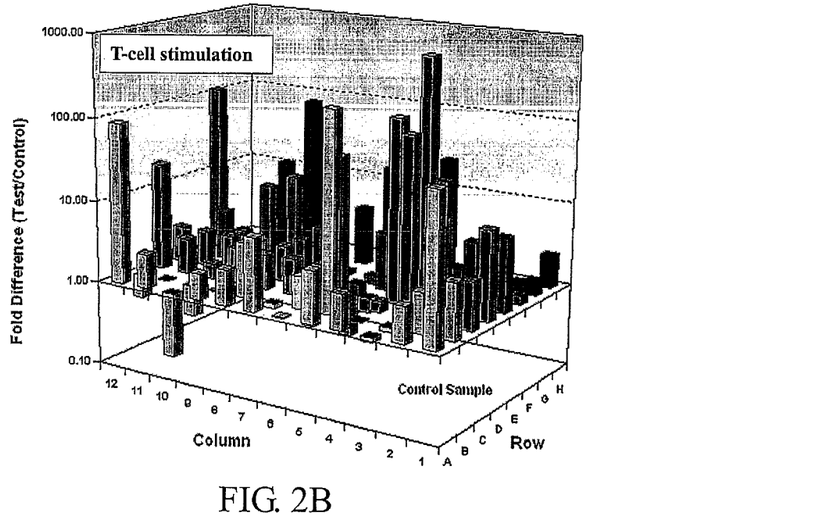
Figure 2C:
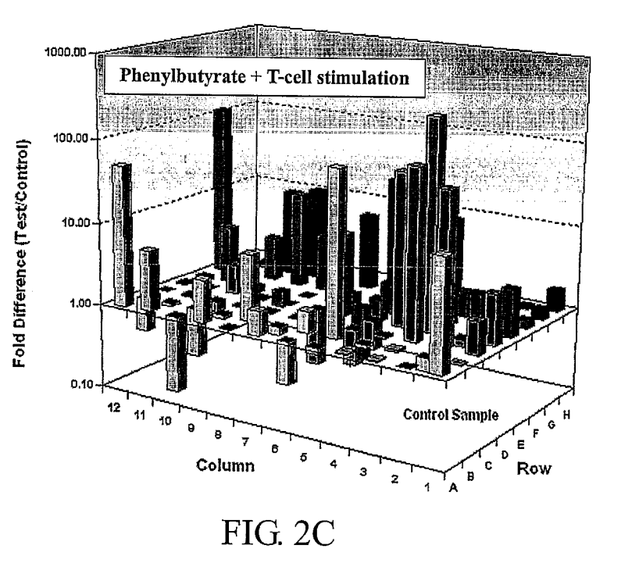
Figure 2D:
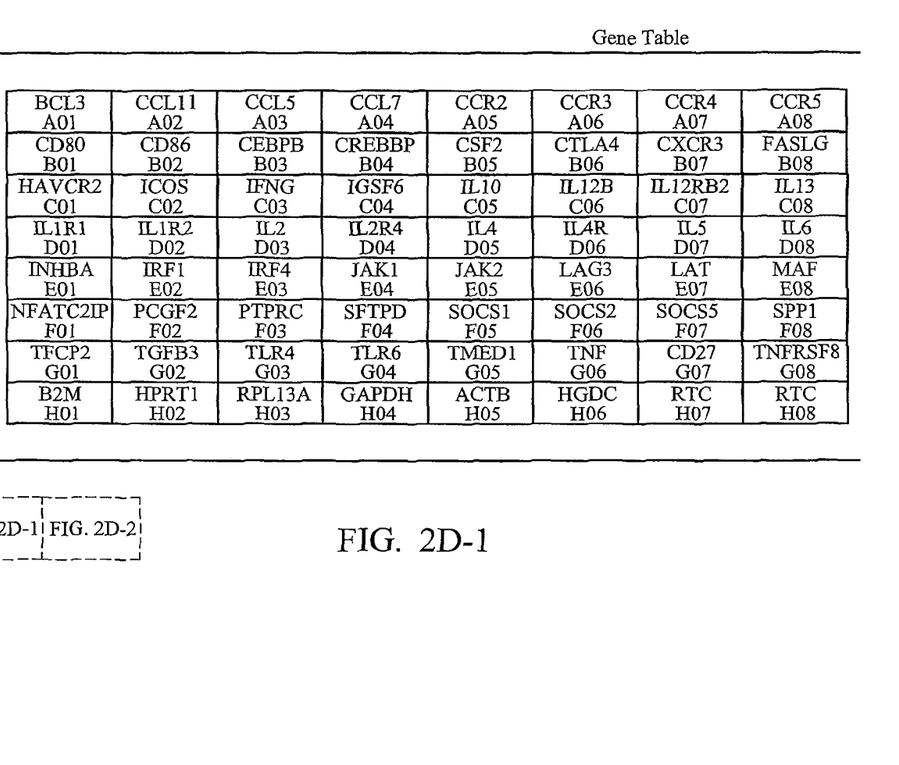
Figure 2D:
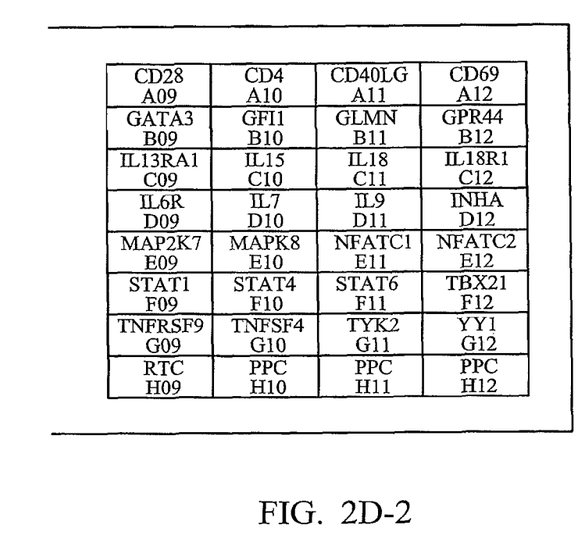

Referring to FIG. 1, the 2.5% phenylbutyric acid gel rapidly relieved the itchy sensation within 2-10 minutes, and improved the mean VASs from 7.25, 7, 6.75, 8, and 7.75 to 2, 1, 1.5, 2.5 and 2.25 in 1-2 days in patients with radiation-induced dermatitis, sun burn, surgical wound healing, psoriasis, or atopic dermatitis, respectively. The pruritus-related symptoms of erythema, urticaria, swelling, and desqumation also subsided simultaneously.

Example 3

Suppression of Multiple Itching-associated Molecular Mediators by 4-phenylbutyrate Sodium Itching is the most important problem in many allergic and inflammatory skin diseases. The skin barrier (stratum corneum) is a major factor for determining the nature of immune responses to allergens presented at the skin surface.

Abnormalities in skin barrier function may result in Th1, Th2 and Th3 responses to infectious agents, chemicals, or protein antigens, which induce several cytokines and molecular mediators in the skin lesion to cause symptoms and signs of pruritus. The cytokine profile subsequently produced depends upon the type of allergen stimulation. Distinct subsets of helper T cell activation have been identified by virtue of cytokines that they produce. Activated Th1 cells produce IFN-gamma and IL-2. Th1 cells regulate delayed type hypersensitivity reactions. Th1 responses are promoted by local release of the IL-12 superfamily of cytokines. These responses are further enhanced by IL-15 and IL-18 production. Activated Th2 cells produce IL-4 and IL-10. Th2 cells mediate allergic and antibody responses. Th2 responses are favored by local production of IL-4, IL-33, and IL-18 in synergy. Some cytokines, such as IL-3, GM-CSF (CSF2), and TNF-alpha, are produced by both Th1 and Th2 subsets. On the other hand, IL-6 is a pro-inflammatory cytokine secreted by activated T cells to stimulate immune response to trauma, especially burns or other tissue damage leading to inflammation. Th3 cells are related to negative regulation of immune response.

In order to demonstrate whether phenylbutyrate can suppress multiple itching-associated cytokines, molecular mediators or markers at one time, a panel of gene expression profiling was analyzed by using real-time PCR (RT$^2$ Profiler™ PCR Array Human Th1-Th2-Th3: APHS-034, SuperArray Bioscience Corporation).

Jurkat T cells were treated in the presence of increasing concentrations of 4-phenylbutyrate, ionomycin, and/or phorbol 12-myristate 13-acetate (PMA) for 24-72 hr at 37° C. At the doses of 1 mM of 4-phenylbutyrate for 48 hrs, and 1 μM of ionomycin plus 10 ng/ml of PMA incubated for 24 hrs, no significant differences were found by flow cytometry in cell proliferation, cytotoxicity, and apoptosis between control and treated cells. However, 48 hrs after stimulation with ionomycin (1 μM) plus PMA (10 ng/ml), T cells were full cycling and progressed through the S, G2, and M phases of the cell cycle due to the induction of T cell growth and survival factors (interleukins), whereas pre-treatment with phenylbutyrate (1 mM) for 24 hrs almost completely prevented entry of the cells into the S phase of the cell cycle.

Jurkat T-cells were nonstimulated or stimulated with ionomycin (1 μM) and PMA (10 ng/ml) for 6 hrs in the absence or presence of pre-incubation of 4-phenylbutyrate sodium (1 mM) for 24 hrs, RNA was extracted and then RT-PCR was performed for profiling the expression of 84 genes related to Th1-Th2-Th3 responses shown in the gene table (FIG. 2).

Referring to FIGS. 2A-2D and Table 1, phenylbutyrate completely suppresses or significantly decreases the induction of Th1 cytokines and related genes (CCR5, CSF2, IFN-gamma, IL12B, IL12RB2, IL18, IL18R1, IL2, IL2RA, IRF1, STAT4, TLR4, TLR6), Th2 cytokines and related genes (CCL11, CCL7, CCR2, CCR4, IL13, IL13RA1, IL1R1, IL1R2, IL4R, IL9, IRF4, MAF), T-cell activation markers (BCL3, CD69, IL6, IL6R, JAK2, LAT, TNFRSF9), T-helper 1 type immune response (IL12B, IL18, IRF4, SFTPD, TLR4, TLR6), T-helper 2 type immune response (IL18, IL4R, IRF4), and antimicrobial humoral response (CCL7, CCR2, IL12B, IL13, SFTPD) in PMA/ionomycin-induced Jurkat T-cell activation. On the other hand, phenylbutyrate upregulates more expression of SOCS1, a suppressor of cytokine signaling as a Th3 response, which is involved in negative regulation of cytokines.

IL-1 and IL-6 are pro-inflammatory cytokines. Antigen binding to the T cell receptor stimulates the secretion of IL-2, and the expression of IL-2 receptors. The IL-2/IL-2R interaction then stimulates the growth, differentiation and survival of antigen-selected cytotoxic T cells. IL-4 stimulates activated B-cell and T-cell proliferation, and the differentiation of CD4+T-cells into Th2 cells, and induces B-cell class switching to IgE. IL-9 elicits many functions on lymphoid cells and mast cell lineages, and has been thought to have a role in asthma. IL-12 is known as a T cell stimulating factor in response to antigenic stimulation, which can stimulate the growth and function of T cells. IL-13 secreted by many cell types, but especially Th2 cells, is an important mediator of allergic inflammation. IL-18 works together with IL-12 to induce cell-mediated immunity following infection with microbial products like lipopolysaccharide. Taken, together, the effects of phenylbutyrate on inhibiting the complicated interrelated signaling network pathways of IL-1, IL-2, IL-4, IL-6, IL-9, IL-12, IL-13, and IL-18, and on upregulating SOCS1 (a suppressor of cytokine signaling) are correlated with the novel finding in the present invention that phenylbutyrate has the ability to ameliorate pruritus in some allergic and inflammatory dermatitis-associated pruritus.

TABLE 1

At least 2-Fold difference in induction by T-cell stimulation when compared to control, and suppressive effects of phenylbutyrate

|  | Mitogen stimulation | Phenylbutyrate + mitogen stimulation |
| --- | --- | --- |
| Th1 cytokines and related genes | | |
| CCR5 | 2.68 | 0.98 |
| CSF2 | 229.13 | 88.77 |
| IFN-gamma | 126.24 | 99.18 |
| IL12B | 2.68 | 0.98 |
| IL12RB2 | 2.68 | 0.98 |
| IL18 | 2.68 | 0.98 |
| IL18R1 | 19.97 | 0.98 |
| IL2 | 831.75 | 304.86 |
| IL2RA | 151.17 | 64.98 |
| IRF1 | 5.86 | 1.7 |
| SOCS1 | 4.82 | 8.59 |
| STAT4 | 7.89 | 3.32 |
| TLR4 | 2.68 | 0.98 |
| TLR6 | 29.04 | 10.43 |
| Th2 cytokines and related genes | | |
| CCL11 | 2.68 | 0.98 |
| CCL7 | 2.68 | 1.04 |
| CCR2 | 4.20 | 0.84 |
| CCR4 | 7.41 | 1.93 |
| IL13 | 2.68 | 0.98 |
| IL13RA1 | 2.68 | 0.98 |
| IL1R1 | 11.31 | 3.92 |
| IL1R2 | 2.25 | 0.82 |
| IL4R | 42.81 | 9.53 |
| IL9 | 2.68 | 0.98 |
| IRF4 | 26.17 | 16.50 |
| MAF | 2.68 | 0.98 |
| Other T-cell activation markers | | |
| BCL3 | 58.08 | 19.73 |
| CD69 | 87.43 | 48.57 |
| IL6 | 2.68 | 0.98 |
| IL6R | 2.68 | 0.98 |
| JAK2 | 4.72 | 2.27 |
| LAT | 3.12 | 1.57 |
| SFTPD | 2.68 | 0.98 |
| TNFRSF9 | 89.26 | 13.01 |

Figure 3:
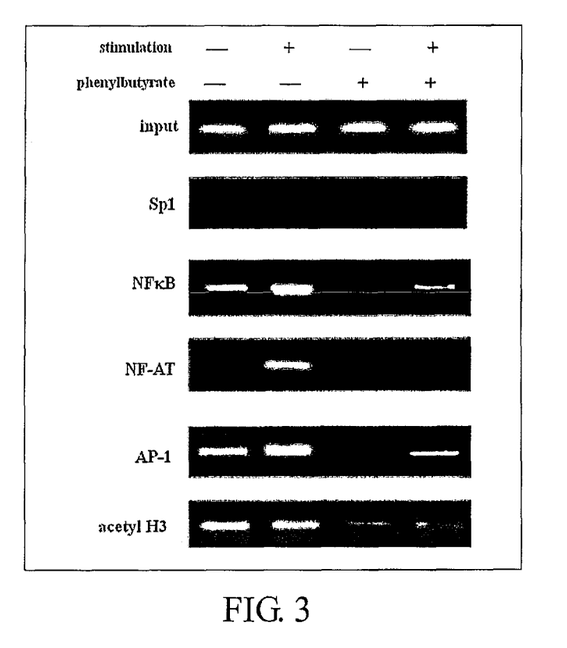
FIG. 3 is a chromatin immunoprecipitation (ChIP) assay demonstrating the modulatory effects of phenylbutyrate on the status of histones that remodel chromatin structure and the binding of transcription-factors that regulate gene expression. Results show that 4-phenylbutyrate sodium was effective in not only modifying histones but also decreasing binding of transcriptional factors of NF-κB, NFAT, and AP-1 to the IL-2 promoter in activated Jurkat T cells stimulated by ionomycin and PMA. Anti-Sp1 antibody was used as a negative control because Sp1 does not bind to IL-2 promoter.

The induction of multiple cytokine expression depends on the coordinated activation of transcription factors, mostly including NFκB, NF-AT, and AP-1 (Sancho R, et al. J Immunol 172:2341-51, 2004; Li-Weber M, et al. Eur J Immunol 34 :1111-18, 2004). Because induction of cytokines is regulated mainly at the transcriptional level, chromatin immunoprecipitation (ChIP) analysis in Jurkat T cells was performed to determine the binding of NFκB, NF-AT, and AP-1 to IL-2 promoter. Jurkat T cells were nonstimulated or stimulated with ionomycin (1 μM) and PMA (10 ng/ml) for 6 hrs in the absence or presence of pre-incubation of 4-phenylbutyrate sodium (1 mM) for 24 hrs, then formaldehyde crosslinking between protein and DNA and ChIP using anti- NFκB, NF-AT, AP-1, Sp1 or acetyl H3 antibodies (Santa Cruz) were performed. PCR primers were designed to amplify the human IL-2 promoter: F 5'-GAGTTACTTTTGTATCCCCACCCCC (SEQ ID NO: 1) (−317 to −292 in the IL-2 promoter), R 5'-CCTGTACATTGTGGCAGGAGTTGAGG (SEQ ID NO: 2) (+33 to 58). PCR amplifications used a three-step protocol with 90° C. (30 s) denaturing temperature, 59° C. (45 s) primer annealing temperature, and 72° C. (30 s) enzyme reaction temperature for 35 cycles. Referring to FIG. 3, phenylbutyrate affects chromatin structure by altering acetyl H3 status, and decreases DNA binding of NFκB, NF-AT, and AP-1 to IL-2 promoter, suggesting the suppression of phenylbutyrate on cytokine expression during T-cell activation could be mediated by decreasing binding of transcriptional factors to promoters.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method of treating or ameliorating pruritus associated with a cutaneous, a mucosal or a systemic disease or disorder, comprising administering to a subject with pruritus or topically applying to an affected area with pruritus an effective amount of a formulation consisting of a short-chain fatty acid derivative of 2 to 6 carbons in length or a pharmaceutically acceptable salt or solvate thereof as an active ingredient, and a pharmaceutically acceptable carrier, wherein the short-chain fatty acid derivative is selected from the group consisting of butyric acid, butyrate, 2,2 dimethyl butyric acid, a-methylhydrocinnamic acid, 3,5 dimethoxy-4-hydrocinnamic acid, cinnamic acid, butyryl hydroxamate, propionate, bromopropionate, E-3-3 pyridyl-2-propenoic acid, levulinic acid, Kemp triacid, isovalerate, valerate, butyramide, isobutyramide, valproic acid, and valproate.

2. The method as claimed in claim 1, wherein the disease or disorder is selected from the group consisting of allergic dermatoses, pruritic dermatoses, vascular dermatoses, sebaceous gland disorders, autoimmune disorders, rheumatoid arthritis, systemic lupus erythematosus, progressive systemic sclerosis, sjogren's syndrome, dermatomyositis, mixed connective tissue disease, papulosquamous dermatoses, bacterial dermatoses, viral dermatoses, mycolic skin infections, granulomatous dermatoses, parasitic skin dermatoses, exfoliative dermatitis, bullous dermatoses, pigmented dermatoses, photosensitive dermatoses, dermatoses caused by collagen diseases, dermatoses due to internal diseases, xerosis, urticaria, atopic dermatitis, eczyma, vasculitis, lichen simplex chronicus, psoriasis, scabies, pediculosis corporis and pubis, multiple sclerosis, thyrotoxicosis, diabetes, renal insufficiency, uremia, iron deficiency anemia, cholestasis, delusions of parasitosis, polycythemia rubra vera, wound, sun burn, cold sores, acne, insect bite, radiotherapy or chemotherapy-induced dermatitis or mucositis, paraneoplastic syndrome, malignancy, primary skin cancer, and metastatic skin cancer.

3. The method as claimed in claim 1, wherein the short-chain fatty acid derivative is present in an amount from about 0.00001% to about 100.00% by weight of the formulation.

4. The method of claim 1, wherein the formulation is formed into a cream, a gel, a lotion, a paste, an ointment, an emollient, a liposome, a nanosphere, a skin tonic, a mouth wash, an oral rinse, a shampoo, a mousse, a spray, a pack, a capsule, a tablet, a powder, a granule, a solution, a suspension, a patch, an occlusive skin conditioning agent, or a patch-type administering apparatus with micro needles.

5. The method of claim 1, wherein the formulation further comprises a penetration enhancing agent, or a pH adjusting agent to provide a formulation pH in the range of approximately 3.0 to 13.0.

6. The method of claim 1, wherein the formulation is administered in combination with a second agent comprising an anti-histamine, an anticholinergic, a non-steroid anti-inflammation drug, a steroid, an anti-oxidant agent, a vitamin, a leukotriene modifier, an interleukin antagonist, a mast cell inhibitor, an antiIgE antibody, a selective serotonin reuptake inhibitor (SSRI), a 5-hydroxytryptamine (5-HT) receptor antagonist, an antibiotic, a calcineurin inhibitor, a histone deacetylase inhibitor, a gastrin-releasing peptide receptor antagonist, gabapentin, naloxone, or a combination thereof.

7. The method of claim 6, wherein the formulation and the second agent are systemically or topically administered simultaneously or sequentially.

8. A method of treating or ameliorating pruritus associated with a cutaneous, a mucosal or a systemic disease or disorder, comprising administering to a subject with pruritus or topically applying to an affected area with pruritus an effective amount of a formulation consisting of phenylbutyric acid or a pharmaceutically acceptable salt or solvate thereof as an active ingredient, and a pharmaceutically acceptable carrier.

9. The method of claim 8, wherein the pharmaceutically acceptable salt is a pharmaceutically acceptable base addition salt, the base being selected from the group consisting of an inorganic bases cation, dicyclohexylamine, a methyl-D-glucamine, an amino acid, a low molecular weight alkylamine, a basic nitrogen-containing alkyl halide, a basic nitrogen-containing dialkyl sulfate, and a basic nitrogen-containing asthma halide.

10. The method of claim 8, wherein the disease or disorder is selected from the group consisting of allergic dermatoses, pruritic dermatoses, vascular dermatoses, sebaceous gland disorders, autoimmune disorders, rheumatoid arthritis, systemic lupus erythematosus, progressive systemic sclerosis, sjogren's syndrome, dermatomyositis, mixed connective tissue disease, papulosquamous dermatoses, bacterial dermatoses, viral dermatoses, mycolic skin infections, granulomatous dermatoses, parasitic skin dermatoses, exfoliative dermatitis, bullous dermatoses, pigmented dermatoses, photosensitive dermatoses, dermatoses caused by collagen diseases, dermatoses due to internal diseases, xerosis, urticaria, atopic dermatitis, eczyma, vasculitis, lichen simplex chronicus, psoriasis, scabies, pediculosis corporis and pubis, multiple sclerosis, thyrotoxicosis, diabetes, renal insufficiency, uremia, iron deficiency anemia, cholestasis, delusions of parasitosis, polycythemia rubra vera, wound, sun burn, cold sores, acne, insect bite, radiotherapy or chemotherapy-induced dermatitis or mucositis, paraneoplastic syndrome, malignancy, primary skin cancer, and metastatic skin cancer.

11. The method of claim 8, wherein the phenylbutyric acid is present in an amount from about 0.00001% to about 100.00% by weight of the formulation.

12. The method of claim 8, wherein the formulation is formed into a cream, a gel, a lotion, a paste, an ointment, an emollient, a liposome, a nanosphere, a skin tonic, a mouth wash, an oral rinse, a shampoo, a mousse, a spray, a pack, a capsule, a tablet, a powder, a granule, a solution, a suspension, a patch, an occlusive skin conditioning agent, or a patch-type administering apparatus with micro needles.

13. The method of claim 8, wherein the formulation further comprises a penetration enhancing agent, or a pH adjusting agent to provide a formulation pH in the range of approximately 3.0 to 13.0.

14. The method of claim 8, wherein the formulation is administered in combination with a second agent comprising an anti-histamine, an anticholinergic, a non-steroid anti-inflammation drug, a steroid, an anti-oxidant agent, a vitamin, a leukotriene modifier, an interleukin antagonist, a mast cell inhibitor, an antiIgE antibody, a selective serotonin reuptake inhibitor (SSRI), a 5-hydroxytryptamine (5-HT) receptor antagonist, an antibiotic, a calcineurin inhibitor, a histone deacetylase inhibitor, a gastrin-releasing peptide receptor antagonist, gabapentin, naloxone, or a combination thereof.

15. The method of claim 14, wherein the formulation and the second agent are systemically or topically administered simultaneously or sequentially.

* * * * *